US008343298B2

(12) United States Patent
Rawlings et al.

(10) Patent No.: US 8,343,298 B2
(45) Date of Patent: Jan. 1, 2013

(54) AIRCRAFT STRUCTURES BONDED WITH ADHESIVE INCLUDING MAGNETOSTRICTIVE MATERIAL

(75) Inventors: Diane C. Rawlings, Bellevue, WA (US); Robert J. Miller, Fall City, WA (US); Kenneth A. Krienke, Seattle, WA (US); James H. Mabe, Seattle, WA (US); Robert T. Ruggeri, Kirkland, WA (US); Dan J. Clingman, Auburn, WA (US)

(73) Assignee: The Boeing Company, Chicago, IL (US)

( * ) Notice: Subject to any disclaimer, the term of this patent is extended or adjusted under 35 U.S.C. 154(b) by 1373 days.

(21) Appl. No.: 11/956,216

(22) Filed: Dec. 13, 2007

(65) Prior Publication Data

US 2012/0305167 A1 Dec. 6, 2012

(51) Int. Cl.
B29C 65/00 (2006.01)
B32B 37/00 (2006.01)

(52) U.S. Cl. ................................. 156/272.4; 156/272.2

(58) Field of Classification Search ............... 156/272.2, 156/272.4
See application file for complete search history.

(56) References Cited

U.S. PATENT DOCUMENTS 5,453,291 A * 9/1995 Sasahara et al. ................... 427/8
5,641,422 A 6/1997 Matsen et al.
5,833,795 A * 11/1998 Smith et al. ................. 156/272.4
6,127,822 A * 10/2000 Sasahara et al. ............... 324/209
6,849,195 B2 2/2005 Basheer
7,534,319 B2 * 5/2009 Mead et al. .................... 156/259
2008/0128649 A1 * 6/2008 Mehrotra et al. .......... 252/62.54

FOREIGN PATENT DOCUMENTS

DE 103 22 055 A1 12/2004
JP 06-155583 A 6/1997

OTHER PUBLICATIONS

Chen et al., "Health monitoring of composites embedded with magnetostrictive thick film without disassembly," Inst. of Physics Publishing, SmartMater.Struct.15 (2006) pp. 20-32.*
Chen et al., "Metal-bonded Co-Ferrite Composites for Magnetostrictive Torque Sensor Applications" IEEE Transactions on Magnetics, vol. 35, No. 5, (Sep. 1999), pp. 3652-3654.
Chen et al.,"Health monitoring of composites embedded with magnetostrictive thick film without disassembly," Inst. of Physics Publishing, SmartMater.Struct.15(2006) 20-32.
Grimes et al., "Wireless Magnetoelastic Resonance Sensors: A Critical Review" Sensors 2002, 2, 294-313.
Pasquale et al., "Stress sensing with Cobased ferrite composites," Journal of Magnetism and Magnetic Materials 242-245 (2002) 1460-1463.
Saravanos et al., "Detection of Delaminations in Composite Beams Using Piezoelectric Sensors," NASA Technical Memorandum 106611 (Jun. 1994).
Tan et al.,"Delamination Detection of a Laminated Beam Using Magnetostrictive Composite Sensor and Actuator," Journ. of Reinforced Plastics & Composites, 26-8 (2007) 831-46.

* cited by examiner

Primary Examiner — Khanh P Nguyen
Assistant Examiner — Carson Gross

(57) ABSTRACT

First and second aircraft structures are bonded together with an adhesive including strain-sensitive magnetostrictive material.

13 Claims, 3 Drawing Sheets

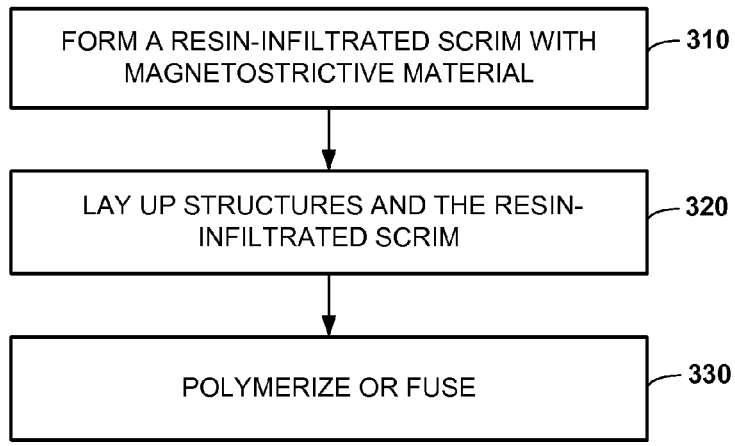
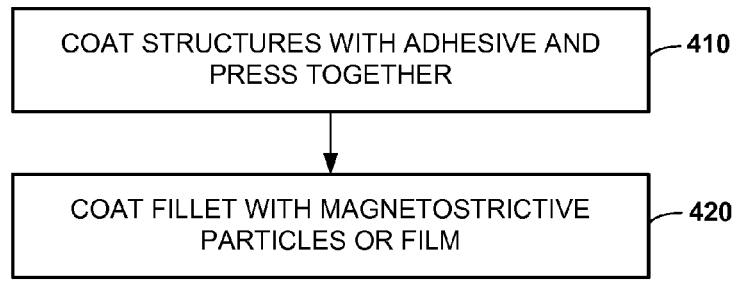
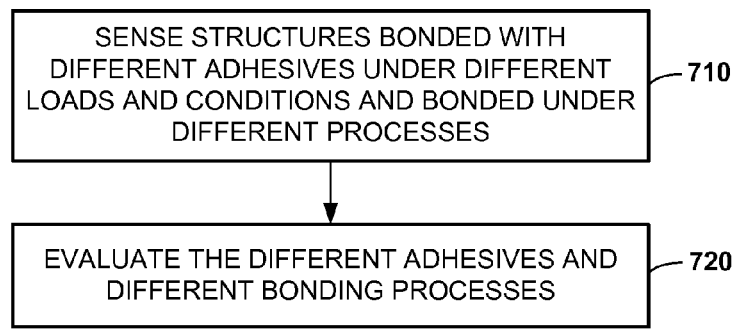

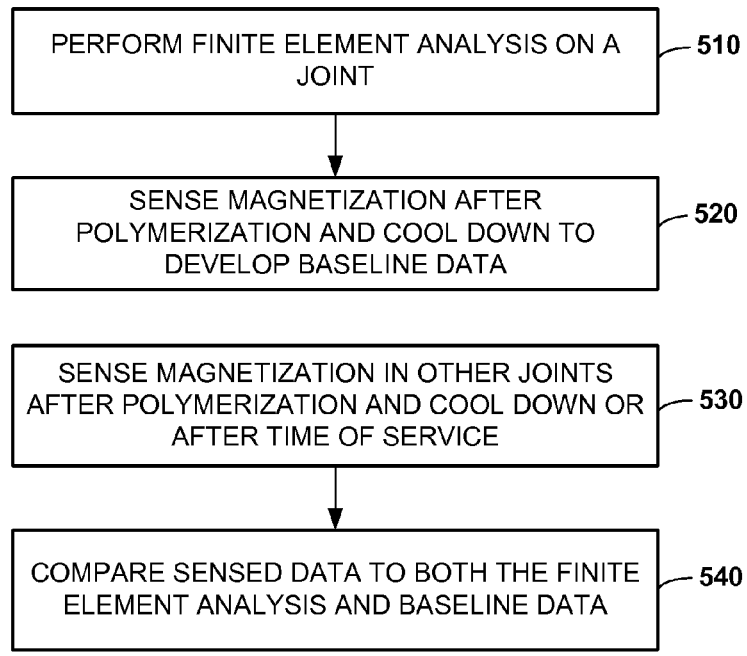
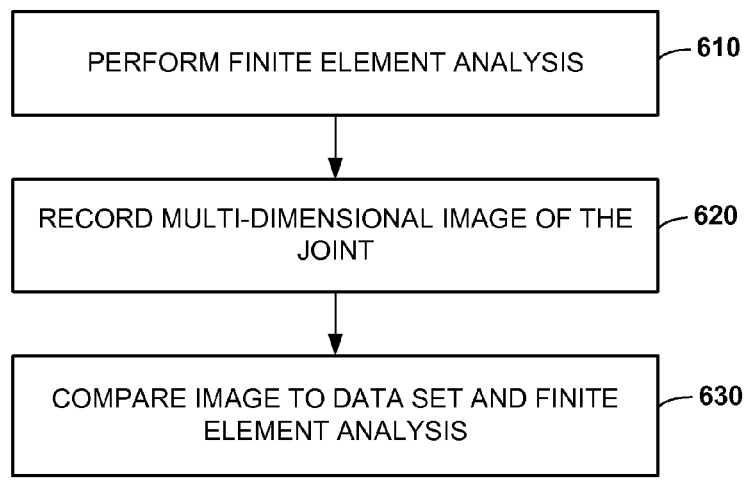

AIRCRAFT STRUCTURES BONDED WITH ADHESIVE INCLUDING MAGNETOSTRICTIVE MATERIAL

BACKGROUND

Lightweight composite materials hold great promise for the aircraft industry. Fiber composites provide a significant improvement in specific strength and stiffness over conventional metal alloys. Better specific strength and stiffness translates into weight savings, which translates into fuel savings and lower operating costs. Additionally, composites do not corrode like aluminum, and they are more resistant to fatigue.

Composite elements such as skins, stiffeners, frames and spars are joined together to form major components such as wings, fuselage and empennage. The composite elements may be bonded together with polymeric adhesive. In theory, adhesive bonds alone have sufficient strength and integrity to support loading of these components. Therefore, adhesive bonds should be able to greatly reduce the number of metal fasteners in the major components.

In practice, however, certain federal aviation regulations require substantiation that a bonded joint between any two primary structural components will carry a specified load with a maximum disbond (that is, where an entire bond line is missing). One solution to this lack of confidence in adhesively bonded joints has been to add metal fasteners. If an adhesively bonded joint fails, a metal fastener would continue holding the joint together.

The use of metal fasteners adds weight to aircraft components. The use of metal fasteners with composite structures also increases the time, cost and complexity of fabrication. High precision machines and complex procedures are used to drill through composite structures. Moreover, penetrations for fasteners provide unwanted paths for lightning strike and corrosion.

Weight is also added by plies of composite that are added around the drilled holes to satisfy requirements for by-pass bearing loads. The additional plies also increase cost of an aircraft. The presence of fastener holes also forces the selection of composite ply layup orientations that reduce the strength of panels and bonded joints (as compared to optimally designed panels and joints without fasteners).

It is believed that adhesive bonds alone, if properly designed, prepared and controlled, have sufficient strength and integrity to bond primary structures together. However, data proving consistency and reliability is unavailable, and current inspection techniques are inadequate to establish confidence in adhesive bonds.

SUMMARY

According to an embodiment of the present invention, first and second aircraft structures are bonded together with an adhesive including strain-sensitive magnetostrictive material.

BRIEF DESCRIPTION OF THE DRAWINGS

FIGS. 2-4 are illustrations of fabrication methods in accordance with embodiments of the present invention.

FIGS. 5-7 are illustrations of methods of using adhesives containing magnetostrictive material in accordance with embodiments of the present invention.

DETAILED DESCRIPTION

Figure 1:
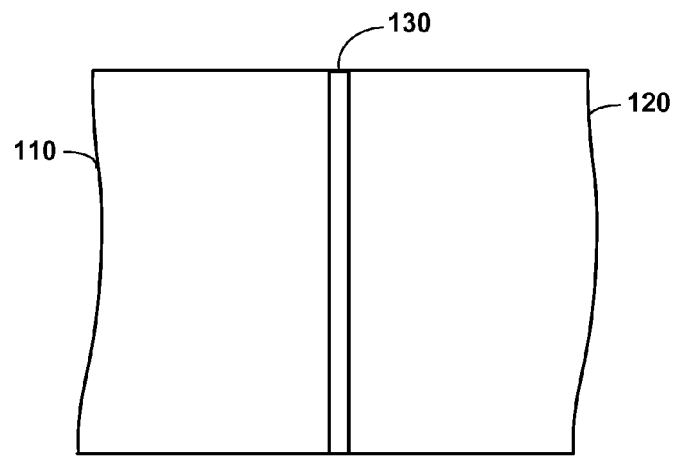
FIG. 1 is an illustration of two aircraft structures and adhesive in accordance with an embodiment of the present invention.

Reference is made to FIG. 1. First and second aircraft structures 110 and 120 are bonded together with an adhesive 130. The aircraft structures 110 and 120 are not limited to any particular types. The structures 110 and 120 may include elements such as skins, stiffeners, frames and spars. The structures 110 and 120 may include major components (or portions thereof) such as wings, fuselage and empennage. The first and second structures 110 and 120 may be primary structures or non-primary structures. They may have the same composition (e.g., composite materials, metal, plastic), or they may have different compositions.

The adhesive 130 may be a thermosetting polymer or a thermoplastic polymer. The adhesive 130 may contain additional materials such as fiber mats (scrim) or other fillers. The adhesive 130 may form a bond line, a fillet, a sealant, a covering on a panel, etc., or it may bridge a bonded joint. The adhesive 130 may be used for bonding primary or non-primary structures.

The adhesive 130 includes strain-sensitive magnetostrictive material. Magnetostriction is a property of ferromagnetic materials that causes the ferromagnetic materials to change their shape when subjected to a magnetic field. Conversely, subjecting magnetostrictive material to any level of physical strain (down to a few microstrains or better) produces a measurable change in its magnetization.

The level of strain in the adhesive 130 is used as an indicator of the strength of adhesion between the adhesive 130 and the structures 110 and 120. Strain in the adhesive 130 develops as the result of chemical and physical changes occurring during polymerization and as the result of coefficient of thermal expansion differences between the adhesive 130 and the structures 110 and 120. The strain in the adhesive 130 can be predicted by finite element analysis. If the bonded joint is without irregularities, the strain map of the joint should match the finite element analysis. Higher levels of adhesive strain should exist in regions of an adhesive 130 with high bond strength due to the stress being applied to the adhesive 130 through its strong (load-carrying) connection to the structures 110 and 120. Lower levels of adhesive strain (as compared to the finite element analysis) will appear in areas within the structure-adhesive interfaces that are in direct contact, but not able to transfer the load without dimensional change (i.e., through a lower modulus material). This will result in a localized measurable difference in the magnetic properties between the localized area and any of a) the strains at other areas, b) computed or expected strains, c) the same area at another time, and d) the same area after damage. Lower strain levels indicate the presence or predisposition for irregularities such as disbonds, delaminations, and localized cavitation (on the order of 10-100 microns).

By measuring localized differences in magnetic properties, lower levels of strain can be located. For instance, "kissing disbonds" occur where the adhesive 130 and structure surfaces are in contact, but load is not transferred across the interface under loading of the joint. Kissing disbonds may occur due to the presence of low modulus regions of contaminants such as siloxane release agents.

The magnetostrictive material is not limited to any particular composition. In some embodiments, the magnetostrictive material may include magnetic metal oxides such as magnetite, amorphous metals, and ferromagnetic metals and alloys such as nickel-iron (NiFe). In some embodiments, the magnetostrictive material may also include ferrites or oxides of ferromagnetic metals or alloys.

In some embodiments, the magnetostrictive material may include Terfenol-D. Terfenol-D is an alloy of terbium, dysprosium, and iron metals. It is a solid-state transducer capable of converting very high energy levels from one form to another. In the case of electrical-to-mechanical conversion, the magnetostriction of Terfenol-D generates strains 10 to 20 times greater than traditional magnetostrictive materials such as iron-cobalt alloys, and two to five times greater than traditional piezoceramics. Terfenol-D has a high Curie temperature (380° C.), which enables magnetostrictive performance greater than 1000 ppm from room temperature to 200° C. Common service temperatures of an aircraft might be in the range from −65° F. to 300° F., with some resin systems being used outside of this range. Some parts of an aircraft may remain hot even when flying at altitude due to proximity to engines or heat given off by internal aircraft systems in confined areas.

In some embodiments, the magnetostrictive material may include Galfenol, which is an iron-gallium alloy that has physical and magnetic properties that are distinctly different than those of Terfenol-D. While Galfenol's magnetostriction is only a third to a quarter that of Terfenol-D, Galfenol is a much more robust material, allowing it to be used in mechanically harsh environments with minimal shock hardening.

Thickness of the adhesive 130 will depend upon the structures being bonded. For instance, a bond line may have a thickness of about 10 mils.

The magnetostrictive material may have a form ranging from nanoparticles to films. Particles such as flakes, fiber shapes and coated fibers typically have higher coupling and therefore are desirable. Particle size and film thickness may be determined by the size and thickness limits allowed by the adhesive 130. However, particle dimensions should be small enough to minimize adverse affects on adhesive structural properties. Still, there is a wide range of useful particle dimensions depending on the shape, ranging from nanometers to microns. Magnetostrictive film thicknesses may range from nanometers to a few microns.

Proportion of the magnetostrictive material to adhesive 130 may be in the range of 0.1% to 30% by volume. However, lower proportions in the range of 0.1% to 1% volume are desirable for adhesive mechanical performance and lower weight.

In some embodiments, the magnetostrictive material (e.g., particles) may be applied to an entire bonded joint. In other embodiments, there might be interest in only a region of the adhesive, whereby the magnetostrictive material is applied only to that region. For example, instead of applying magnetostrictive material to an entire bond line, the magnetostrictive material is applied only to those regions where strains are high and where cavitation and debonding are likely to occur. For typical lap joint configurations, one such region is the area under or adjacent to the adhesive fillet.

Strain in a bonded joint causes strain in the magnetostrictive material. This strain, in turn, produces measurable changes in the magnetization of the magnetostrictive material.

A magnetic sensor may be used to detect a change in strain in the adhesive 130 by measuring changes in magnetization of the magnetostrictive material. The magnetic sensor may include, for example, a magnetic field generating coil ("driving" coil). A non-contacting driving coil operating either at DC or an alternating frequency can create an external magnetic field over the adhesive 130 and it can set the magnetization of the magnetostrictive material. The magnetic sensor may further include an instrument for measuring the resulting magnetic field, which is affected by the magnetostrictive material. The measuring device may include, for example, another coil (a "sensing" coil) or a giant magneto resistance sensor. The magnetization of the magnetostrictive material is sensed and compared to base line data (e.g., a previous measurement of the magnetization, or an expected value representing a good bond). For instance, a driving magnetic coil produces an external magnetic field. The magnetization of the particles changes when the particles are subjected to this external magnetic field. The external magnetic field also produces an electric voltage in the sensing coil. The voltage in the sensing coil changes when the magnetization of the particles change. The magnetic field and this electric voltage are affected by strain on the magnetostrictive material. The electric voltage can be measured. The driving and sensing magnetic coils can be very small in order to have a response to only a small area of a bond. The sensor can scan over the bond to inspect the bond. In some embodiments, the sensor may include an array of driving and sensing coils to produce an image of the bond. The sensor's field of view would be chosen to match the desired resolution (how small of an area to detect).

An advantage of incorporating strain sensitive magnetostrictive material in adhesive is that areas of high and low adhesive strains in the adhesive can be sensed and measured nondestructively. Thus, the strains can be sensed and measured without harming or significantly disassembling the structures 110 and 120 or the adhesive 130.

Another advantage of incorporating strain sensitive magnetostrictive material in adhesive is that areas of weak bonds (e.g., bonds that are weakened due to the presence of contaminants) can be detected. In contrast, conventional nondestructive inspection such as ultrasonic inspection can only detect disbonds, and relatively large voids, bubbles and defects in bond lines, and cannot supply information about the strength of the bond.

Strain can be sensed without having to attach wires to the structures 110 and 120, and without having wires stick out of the structures 110 and 120 or the adhesive 130. Wires sticking out the adhesive 130 are undesirable as they would create a pathway for moisture or fluids from the atmosphere surrounding the joint to move into the interior of the adhesive and thereby increase the chances for premature joint failure.

Figure 2:
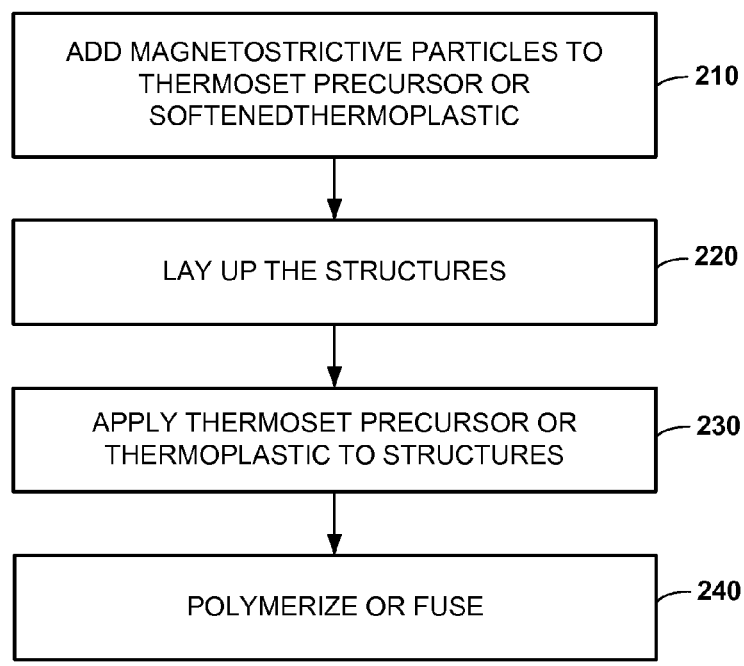

The bonding of the structures 110 and 120 is not limited to any particular method. FIGS. 2-4 illustrates some examples.

Reference is now made to FIG. 2. In some embodiments, magnetostrictive particles are distributed uniformly in the adhesive. For an adhesive such as a thermosetting polymer, the magnetostrictive material may be added to polymer precursors (block 210). Examples of polymer precursors include a resin, a low molecular weight polymer, and monomers. In typical two-part epoxy adhesive/resin systems the magnetostrictive particles may be mixed with one or both components, either prior to mixing the reactants together or afterwards. The structures are laid up (block 220), the mixture is either placed between or physically applied to one or two structures (block 230), and the layup is placed in a vacuum bag and cured in a press or autoclave (block 240). In some embodiments, the adhesive containing magnetostrictive material could be co-cured with a lay-up of prepreg material. The adhesive with magnetostrictive material could be used as resin for the composite pre-preg. In other embodiments such adhesive may be used in a secondary bonding process to bond two previously cured composite structures or metallic/metallic or composite/metallic structures.

For an adhesive such as a thermoplastic polymer, the magnetostrictive particles can be added during manufacture of the thermoplastic polymer or mixed in by standard compounding and extrusion techniques after the thermoplastic polymer is softened (block 210). The structures are laid up (block 220), and a film of thermoplastic polymer is inserted between the structures (block 230). The thermoplastic polymer is fused (block 240), during which the thermoplastic polymer is heated so it flows and makes intimate contact with the surfaces of the structures, and then allowed to cool so it hardens.

Reference is now made to FIG. 3. In some embodiments, the magnetostrictive particles may be used with a scrim. A scrim may be used to ensure that adhesive is not squeezed out during bonding. A scrim may also be used to support and assist in the handling of an uncured adhesive film. At block 310, a resin-infiltrated scrim with magnetostrictive material is formed. As a first example, the scrim is infiltrated with resin that is filled with magnetostrictive particles. As a second example, the scrim is coated with a thin film of metallic magnetostrictive materials through the use of electroless or electroless and electroplating processes. Then the scrim is infiltrated with resin. As a third example, the scrim is formed from magnetostrictive material.

At block 320, the structures and the resin-infiltrated scrim are laid up. As a first example, the scrim is placed between the surfaces to be bonded. As a second example, the scrim is placed adjacent to the edges of a bonded doubler or part in the region where an adhesive fillet typically forms and where high bond stresses initially develop.

At block 330, the resin is polymerized or fused. The resulting polymeric adhesive contains the scrim. Since the scrim might be more effectively coupled to the adhesive than discrete particles, the scrim might be better able to transfer strain to the magnetostrictive material and result in a more sensitive use of a given weight of magnetostrictive material.

Reference is now made to FIG. 4. In some embodiments, magnetostrictive particles or a magnetostrictive film are coated on adhesive. At block 410, two structures are coated with adhesive and pressed together. Adhesive flows out of the edges to form a fillet around perimeter of bonded joints. The fillet may be formed to a specific shape and surface.

At block 420, the fillet is coated with magnetostrictive particles or a film. The coating may result from the layup of the joint, or it may be applied by a separate operation. Alternatively, a strip of adhesive containing magnetostrictive material may be applied and co-cured adjacent to the perimeter of a bonded doubler or joint in the area where the adhesive fillet will form. Unloaded adhesive bleeding out from the bond line could flow over the surrounding loaded strip of adhesive and bond the two together. A shaped strip of adhesive containing magnetostrictive material may also be incorporated as a fillet or stress minimizing taper.

A method according to an embodiment of the present invention is not limited to applying magnetostrictive material to an entire bond. Magnetostrictive material may be applied only to a specific region. Particles could be formed as a pattern on a surface using standard masking or etching techniques. For example, a surface is masked (e.g., using a photomask), magnetostrictive material is deposited, and then the mask is removed.

A film adhesive may be applied in specific regions. A liquid adhesive or coating of magnetostrictive particles may be applied via spraying or rolling or by draw-down or by transfer coating. A film of magnetostrictive material (e.g., originally created via roll-coating or sputtering or electroplating) may also be incorporated in the layup so long as the film has adequate integrity and the surfaces themselves bond well to the other materials within or surrounding the joint. For example a magnetostrictive film could be formed along with the adhesive fillet to create a way of intimately interrogating the fillet. A magnetostrictive film could be used to coat the carbon fibers of a pre-preg, which would allow excess strain or changes to strain in the composite to be sensed.

A method according to an embodiment of the present invention is not limited to the manufacturing phase. In some embodiments, existing joints could be retro-fitted or repaired. For example, a retrofit or repair might include applying a strip adhesive containing magnetostrictive particles to a bonded joint, or applying an adhesive strip containing a scrim coated with a magnetostrictive film over fillets surrounding a bonded joint.

A method according to an embodiment of the present invention is not necessarily limited to polymeric adhesives. A method according to an embodiment of the present invention may be applied to brazed metal joints, and adhesives that contain non-polymer materials such as fibers, spheres, fillers, etc.

FIGS. 5-7 illustrate different examples of using magnetostrictive material in the adhesive. In the example of FIG. 5, the change in magnetization is sensed as part of process control during manufacture. During polymerization and usually cool-down, the polymers shrink, which results in localized variations in strain levels that depend on the bond strength as well as geometry and material properties. The process control may include performing finite element analysis on a joint (block 510), and sensing the magnetization in the joint after polymerization and cool down to develop baseline data (block 520). Magnetization is then sensed in other joints of other structures after polymerization and cool down or after time in service (block 530). The sensed data of the other joints are then compared to both the finite element analysis and baseline data (block 540). The FEM analysis accounts for differences in geometry and materials, and can represent both the perfect joint and the actual joint. Measurements are compared to baseline to evaluate aging trends. The comparisons will indicate the presence of contamination, part fit-up issues and uneven pressure during cure. The comparisons may also provide feedback about the manufacture process. The feedback can be used to improve the manufacture process.

In the example of FIG. 6, changes in magnetization are sensed in real time as part of aircraft health monitoring. Real time sensing of a realistic number of joints (due to practical limitations of weight, access power, memory, etc.) can be performed wherever a probe can be place in close enough proximity. Adhesive response time to changes in stress might be on the order of seconds or less. At block 610, finite element analysis of a joint is performed. At block 620, the magnetization of a joint may be sensed to record a multi-dimensional (e.g., 2-D or 3-D) image of the joint. At block 630, this image is compared to a set of data and finite element analysis to determine the state of the joint. As a first example, the data set may include 2-D or 3-D reference images of strain for different loads and conditions. The sensed image is compared to the reference images. The comparison indicates how close localized regions of the joint are to critical strain levels. As a second example, measured strain image is compared to a set of allowable changes. The comparison is performed to identify those bonds that have experienced damage or failure initiation and require repair. The comparison may be performed during flight or during on-ground maintenance, as part of periodic inspections of aircraft structures during scheduled visits to repair depots, etc.

In the example of FIG. 7, changes in magnetization are sensed to gain a better understanding about adhesive bonds for aircraft structures. Structures bonded with different adhesives or under different bonding processes are sensed under different loads and conditions (block 710), and the different adhesives or bonding processes are evaluated (block 720). The evaluation provides strain data, which allows the best adhesive to be selected. This data may be compared to computational simulations to strain throughout structural joints and can be used to design improved structural joints. Data can be accumulated to track the structural integrity of "good" adhesive joints over years of heavy use.

The invention claimed is:

1. A method comprising measuring strain in a joint between first and second aircraft structures bonded together with an adhesive, the adhesive including at least one of strain-sensitive magnetostrictive particles, a scrim made of strain-sensitive magnetostrictive material, and a scrim plated with strain-sensitive magnetostrictive material; wherein a magnetic sensor is used to sense a change in magnetization of the adhesive, the change indicating a change in strain in the adhesive, the strain in the adhesive indicating load carrying capability between the adhesive and the structures.

2. The method in claim 1 where the adhesive forms a bond line.

3. The method of claim 1, wherein the adhesive includes the particles.

4. The method of claim 1, wherein the adhesive includes the scrim infiltrated with the particles.

5. The method of claim 1, wherein the adhesive includes the scrim plated with magnetostrictive material.

6. The method of claim 1, wherein the adhesive includes the scrim made of magnetostrictive material.

7. The method of claim 1, wherein the adhesive forms a fillet, and wherein the fillet includes the magnetostrictive particles.

8. The method of claim 2 wherein the magnetostrictive particles are in an adhesive layer adjacent to the bond line so that an adhesive fillet will form over it.

9. The method of claim 2, wherein the adhesive is used in only a region of the bond line.

10. The method of claim 1, wherein the change in magnetization is sensed as part of process control for manufacturing.

11. The method of claim 1, wherein the change in magnetization is sensed as part of aircraft health monitoring.

12. The method of claim 11, wherein the magnetization is sensed to record a multi-dimensional strain image; and wherein the strain image is compared to reference data.

13. The method of claim 1, wherein magnetization changes are sensed to accumulate data to gain a better understanding about different adhesive bonds and different bonding processes for aircraft structures.

\* \* \* \* \*